US007998173B2

(12) United States Patent
Perkins

(10) Patent No.: US 7,998,173 B2
(45) Date of Patent: Aug. 16, 2011

(54) ADJUSTABLE SPINOUS PROCESS SPACER DEVICE AND METHOD OF TREATING SPINAL STENOSIS

(76) Inventor: Richard Perkins, Staatsburg, NY (US)

( * ) Notice: Subject to any disclaimer, the term of this patent is extended or adjusted under 35 U.S.C. 154(b) by 856 days.

(21) Appl. No.: 11/600,321

(22) Filed: Nov. 16, 2006

(65) Prior Publication Data
US 2007/0162000 A1 Jul. 12, 2007

Related U.S. Application Data

(60) Provisional application No. 60/738,930, filed on Nov. 22, 2005.

(51) Int. Cl.
*A61B 17/70* (2006.01)
(52) U.S. Cl. .......................... 606/248; 606/279; 606/250
(58) Field of Classification Search .......... 606/246–249, 606/252, 259–260, 279, 250–251, 253, 261; 623/17.11–17.16
See application file for complete search history.

(56) References Cited

U.S. PATENT DOCUMENTS

| 4,738,251 | A | * | 4/1988 | Plaza | 606/250 |
| 4,998,936 | A | * | 3/1991 | Mehdian | 606/250 |
| 5,133,716 | A | * | 7/1992 | Plaza | 606/250 |
| 5,810,815 | A | * | 9/1998 | Morales | 606/250 |
| 7,083,621 | B2 | * | 8/2006 | Shaolian et al. | 606/86 A |
| 2003/0153915 | A1 | * | 8/2003 | Nekozuka et al. | 606/61 |
| 2006/0106381 | A1 | * | 5/2006 | Ferree et al. | 606/61 |
| 2008/0021466 | A1 | * | 1/2008 | Shadduck et al. | 606/61 |

* cited by examiner

*Primary Examiner* — Eduardo C Robert
*Assistant Examiner* — Steven J Cotroneo
(74) *Attorney, Agent, or Firm* — Perry E. Van Over & Associates, PLLC

(57) ABSTRACT

Provided is an adjustable spacing device configured to be placed between the spinous processes of at least two adjacent vertebrae, the device including a transverse member and at least one adjustable transverse member, which connect two parallel longitudinal legs one to the other and a method of using the device to treat spinal stenosis by restricting extension and allowing normal flexion of adjacent vertebrae relative one to the other.

25 Claims, 8 Drawing Sheets

ADJUSTABLE SPINOUS PROCESS SPACER DEVICE AND METHOD OF TREATING SPINAL STENOSIS

BACKGROUND

1. Technical Field

The present invention relates to devices and methods for use in orthopedic spine surgery. In particular, the present invention relates to an adjustable spacing device configured to be placed between the spinous processes of at least two adjacent vertebrae and a method of using the device to treat spinal stenosis.

2. Background Art

The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions. A healthy intervertebral disc has a great deal of water in the well hydrated nucleus pulposus, the center portion of the disc. The water content gives the nucleus a spongy quality and allows it to absorb spinal stress.

In a young healthy individual, the intervertebral disc also serves as a natural spacer between adjacent vertebrae thus allowing sufficient space in central spinal canal and intervertebral foramina to permit unimpeded nerve passage from the neural canal. In addition to injuries or disease of the intervertebral discs, the common condition of spinal stenosis can impinge upon neural and vascular structures leading to neurological compromise.

Spinal stenosis is a common condition resulting from the narrowing of the spinal canal, nerve root canals and intervertebral foramina causing nerve pinching which leads to persistent pain, lack of feeling and decreased physical activity. Spinal stenosis can be dynamic and postural in that the increased symptoms can be experienced during extension of the spine; such as during standing or walking, and during flexion of the spine, such as bending forward or sitting, can be lessen. Lumbar spinal stenosis is of two general types. The most common is degenerative stenosis, occurring in virtually the entire population as a result of the natural process of aging. It is a degenerative narrowing of the spinal canal, nerve root canals and intervertebral foramina caused by bone and/or ligament hypertrophy in local, segmental or generalized regions. The narrowing of nerve egress pathways from the vertebral column results in compression of spinal nerves and nerve roots, causing a constellation of symptoms, including lower back pain, neurogenic claudication and lower extremity pain. A second general type of spinal stenosis is congenital lumbar spinal stenosis, which is relatively rare and usually presents at an early age, often between 30 and 40. Acquired spinal stenosis is more common and general develops when patients are in their 60's or older. It is a condition that can neither be predicted nor prevented. It does not distinguish by sex, race, or ethnicity. Nor is it associated with any particular occupation or body type.

The most common indication for surgery in persons aged over 60 in the United States is lumbar spinal stenosis. Currently, it is estimated that as many as 400,000 Americans, most over the age of 60, may already be suffering from the symptoms of lumbar spinal stenosis and this number is expected to grow as members of the baby boom generation begin to reach their 60s over the next decade. According to the U.S. Census Bureau, people over 60 will account for 18.7% of the domestic population in 2010 versus 16.6% in 1999. According to the United Nations' Population Division, Department of Economic and Social Affairs, the trend is global with the number of persons aged 60 years or older estimated to be nearly 600 million in 1999 and is projected to grow to almost 2 billion by 2050, at which time the population of older persons will be larger than the population of children (0-14 years) for the first time in human history. The increasing prevalence of musculo-skeletal disorders and the cost to treat them led the World Health Organization and the United Nations to declare that 2000-2010 be the Decade committed to improving quality of life for people with bone and joint disease and injuries throughout the world.

It is this well recognized need to provide relief for a growing population of people suffering from spinal disease or injuries, particularly those suffering from spinal stenosis, that has prompted the increasing effort among orthopedic surgeons to find new methods and devices to provide that badly needed relief.

SUMMARY OF THE DISCLOSURE

Disclosed herein is a device that meets the above identified need by providing a novel device and method for the treatment of spinal stenosis. More particularly, a device is provided that provides an adjustable spacer that can be easily positioned between adjacent spinous processes so as to relieve the pressure between adjacent vertebrae as a treatment for spinal stenosis.

Disclosed is a device for use in the treatment of spinal stenosis that includes an assembly having two approximately parallel elongated legs, the legs being connected one to the other proximate to one end of each leg by a first transverse member and adjustably connected one to the other at a different position along the length of each respective leg by an adjustable transverse member, the first transverse member and the adjustable transverse member each having a shape suitable to abut against a respective spinous process of a vertebrae so as to form a device having a box-like configuration abutted against and between the spinous processes of two adjacent vertebrae.

Also disclosed is a device for the treatment of spinal stenosis that includes an assembly having two approximately parallel elongated legs connected one to the other proximate to one end of each leg by a first transverse member and adjustably connected one to the other one or more different positions along the length of each respective leg by at least one adjustable transverse member each transverse member having a shape suitable to abut against a respective spinous process of a vertebrae so as to form a device having a box-like configuration abutted against and between at least one pair of adjacent spinous processes of respective adjacent vertebrae.

Also disclosed is a device for the treatment of spinal stenosis that includes an assembly having two approximately parallel elongated legs connected one to the other proximate to one end of each leg by a first transverse member and adjustably connected one to the other at multiple different positions along the length of each respective leg by a respective multiple number of adjustable transverse member each transverse member having a shape suitable to abut against a respective spinous process of a vertebrae so as to form a device having a ladder-like configuration with each transverse member being abutted against a respective spinous process.

Also disclosed is a method of treating spinal stenosis that includes providing the device disclosed herein and using surgical methods to position the device on the dorsal side of spinal column of a patient such that the two legs are positioned one on either side of the center of the spinal column and approximately parallel thereto, positioning the first transverse member against the spinous process of a first vertebra and moving the adjustable transverse member to a position abutting against the spinous process of a second vertebra, the second vertebra being adjacent to the first vertebra, locking the adjustable transverse member into position on the two legs so as to form an adjustably fixed spacer between the first spinous process and the second spinous process.

Also disclosed is a method of treating spinal stenosis that includes providing the device disclosed herein and using surgical methods to position the device on the dorsal side of spinal column of a patient such that the two legs are positioned one on either side of the center of the spinal column and approximately parallel thereto, positioning the first transverse member against the spinous process of a first vertebra and moving the multiple, adjustable transverse members to respective positions abutting against the respective spinous process of multiple adjacent vertebrae so as to form a device having a ladder-like configuration.

Also provided is a kit having at least one of the devices disclosed herein and at least one other tool or device useful to the surgical method disclosed herein.

BRIEF DESCRIPTION OF THE DRAWINGS

The foregoing and other features of disclosed device will become apparent to one skilled in the art to which the present invention relates upon consideration of the following description of the invention with reference to the accompanying drawings, wherein.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

Figure 1:
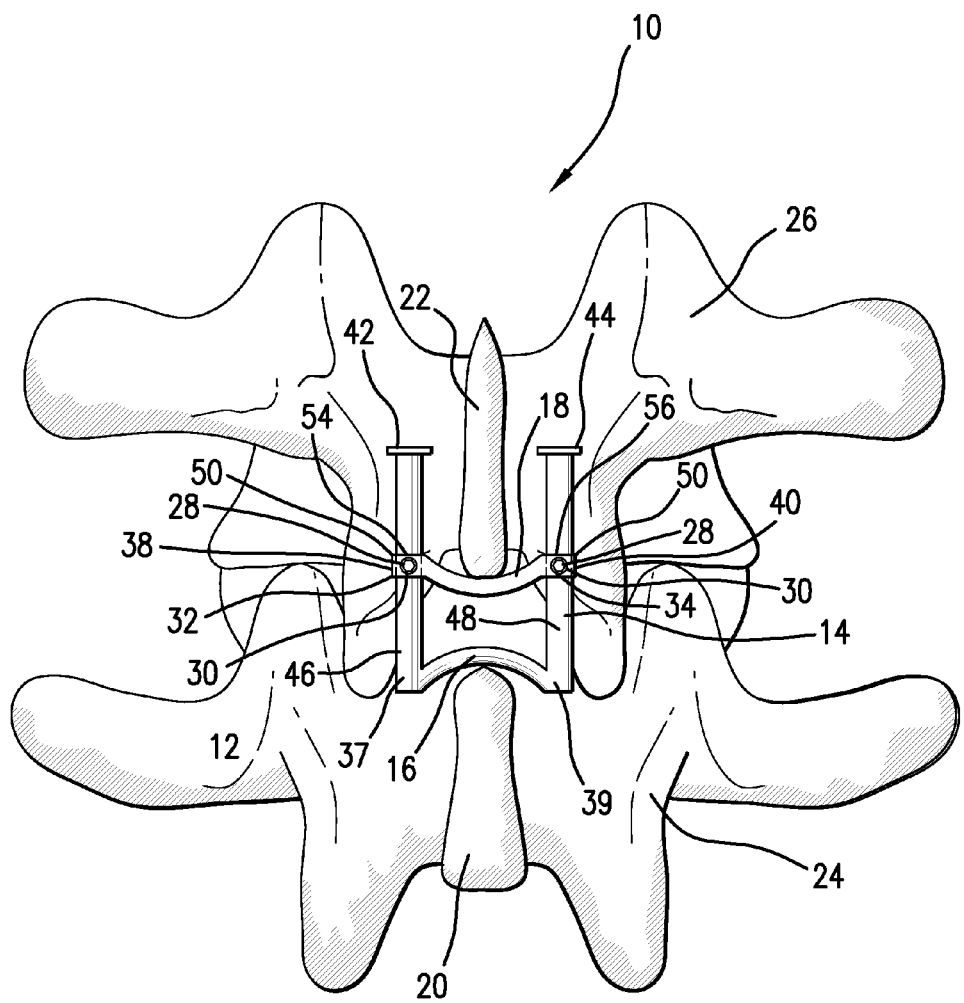
FIG. 1 shows a dorsal view of two adjacent vertebrae having the spinous process spacer device inserted between adjacent spinous processes.

As shown in FIGS. 1-6 and described in the following exemplary description is an adjustable spinous process spacer device, generally shown at 10, which can be used in the treatment of spinal stenosis. The device 10 includes an assembly having a first and a second elongated or longitudinal leg 12, 14, which are in approximately parallel alignment one to the other. The exemplary embodiment described herein is provided with longitudinal legs 12, 14 have a generally circular cross section so as to form a cylindrical form. However, it is within the concept of the invention to provide the device with longitudinal legs 12, 14 having a cross sectional design of any shape along the full or partial length of the leg to include, for example, legs having a square, rectangular, hexagonal, or any other cross sectional design. Further, it is within the concept of the invention that the legs having a cylindrical cross section can also be provided with one or more relatively flat surfaces over at least a portion of the exterior surface of the otherwise cylindrical leg configuration. The legs 12, 14 can be connected one to the other proximate to one end of each leg 12, 14 by a first transverse member 16 and adjustably connected one to the other at a different position along the length of each respective leg 12, 14 by at least one adjustable transverse member 18, the first transverse member 16 and the adjustable transverse member 18 each having a shape suitable to abut against a spinous process 20, 22 of respective vertebrae 24, 26 so as to form an embodiment of the device 10 having a box-like configuration abutted against and between the spinous processes 20, 22 of two adjacent vertebrae 24, 26. This box-like configuration of the device can be releasably locked into place by a transverse member locking device 28. A preferred locking device 28 is a locking element such as, for example, a threaded set screw 30, which can be releasably secured into locking element portals 32, 34 having corresponding threads 36, the locking element portals 32, 34 being located respectively at a transverse member first end 38 and a transverse member second end 40. Each of the longitudinal legs 12, 14 can be terminated by a respective first and second stop member 42, 44. The stop member 42, 44 can be assembled onto the ends of the longitudinal legs 12, 14 by threading, snap fitting, bayonet-fitting, or any other connecting means known in the art. Preferably, the stop member 42, 44 is connected to the longitudinal leg 12, 14 by complementary threading of the stop member 42, 44 into the end of the longitudinal leg 12, 14. A stop member tool receptacle 43, 45 can be defined in the surface of the stop member 42, 44 to facilitate assembly of the stop member 42, 44 to the respective longitudinal leg 12, 14. Without departing from the concept of the invention, the stop member 42, 44 can be provided with a configuration other than the blunt stop member shape shown in FIG. 1. An example of such an alternative to the stop member 42, 44 is the conical shaped end cap 47, 49 shown in FIG. 5. When implanting the device 10 in a patient, the conical shaped end cap 47, 49 can facilitate the piercing of the interspinous ligament. Such a conical shaped end cap 47, 49 can be secured to the respective longitudinal leg 12, 14 by applying an appropriate tool to the tool receiving surfaces 51, 53 provided on the exterior surface of the conical shaped end cap 47, 49. When implanted in a subject, the first and second leg 12, 14 are positioned in relative parallel alignment one to the other along the dorsal surface of the vertebrae and on opposite sides of the spinous processes 20, 22. The first transverse member 16 is abutted against the first spinous process 20 and the adjustable transverse member 28 is firmly abutted against the surface of the second spinous process 22 facing toward the first transverse process 20. In a preferred embodiment of the device 10, the first transverse process at the first end and second end 37, 39 can be fixedly connected at the first end 46 of the first longitudinal leg 12 and at the first end 48 of the second longitudinal leg 14. The adjustable transverse member 18 has a first adjustable end 50 and a second adjustable end 52, each of which is provided with a longitudinal leg through portal 54, 56. These leg through portals 54, 56 are sized and configured to slidably receive the respective first and second longitudinal leg 12, 14. The lumen wall of the through portals 54, 56 respectively define the locking element portals 32 and 34. The assembly of the device 10, as best shown in FIG. 1, when implanted in a subject forms a box-like structure firmly positioned between two adjacent spinous process 20, 22. The longitudinal legs 12, 14 are slidably positioned through the longitudinal leg through portals 54, 56 of the adjustable transverse member 18 and when properly positioned and abutted against the spinous process 22, can be securely held in position by the locking elements 28 which are threadably secured through the locking element portals 32, 34 and tightened against the underlying portion of the respective longitudinal leg 12, 14.

Figure 2:
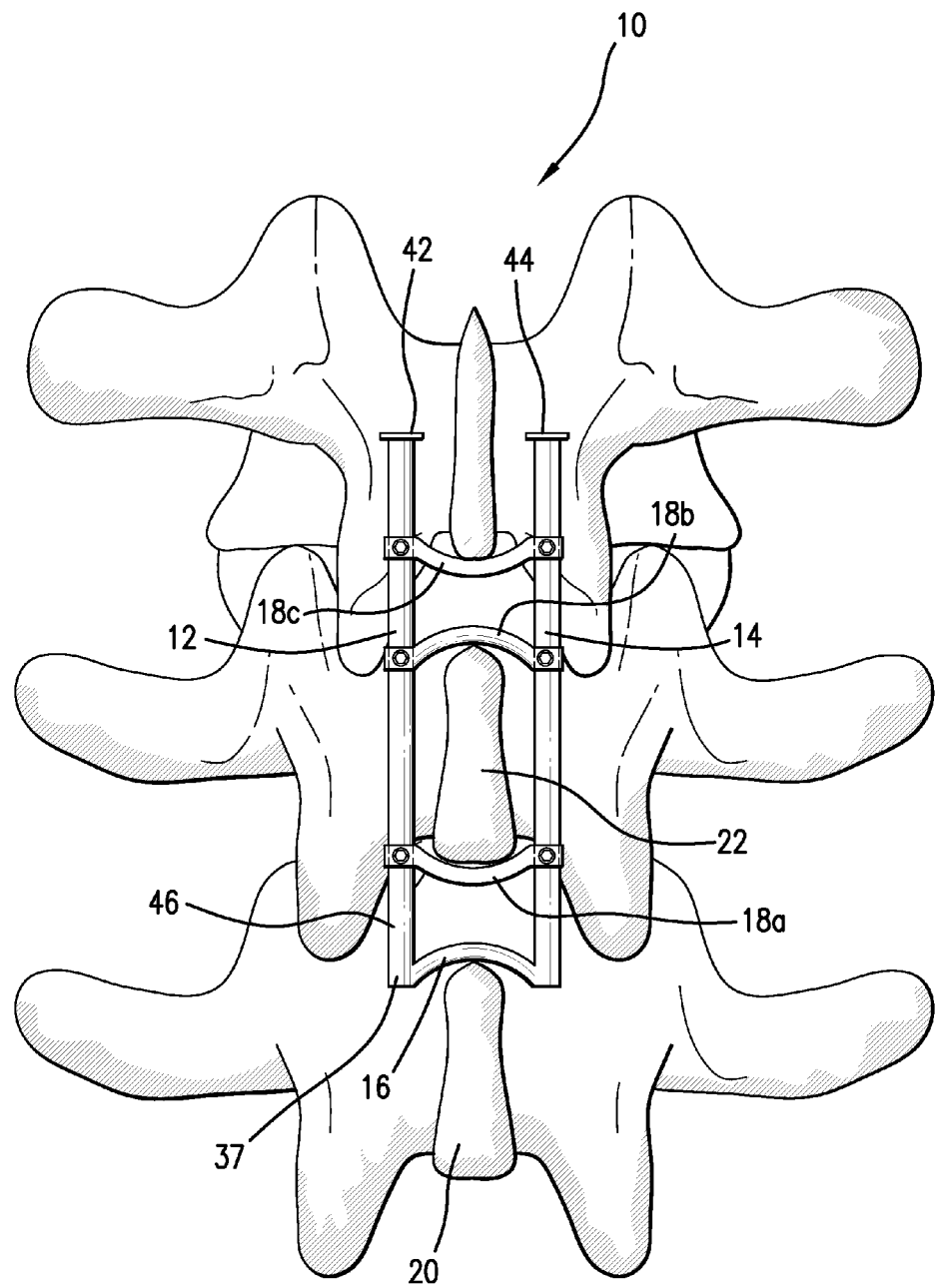
FIG. 2 shows a dorsal view of three adjacent vertebrae having the spinous process spacer device inserted between adjacent spinous processes.
Figure 3:
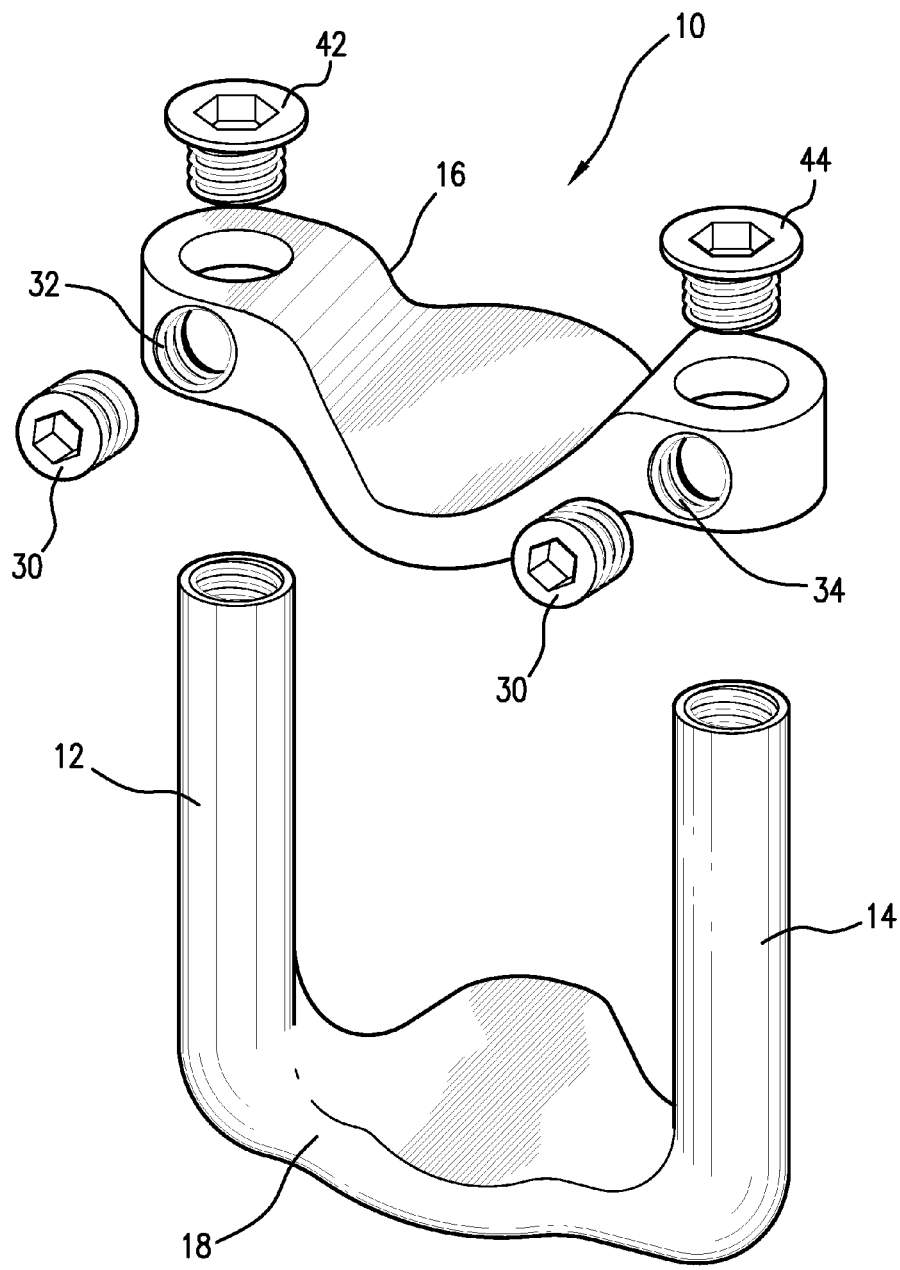
FIG. 3 shows an exploded view of the spinous process spacer device.
Figure 8:
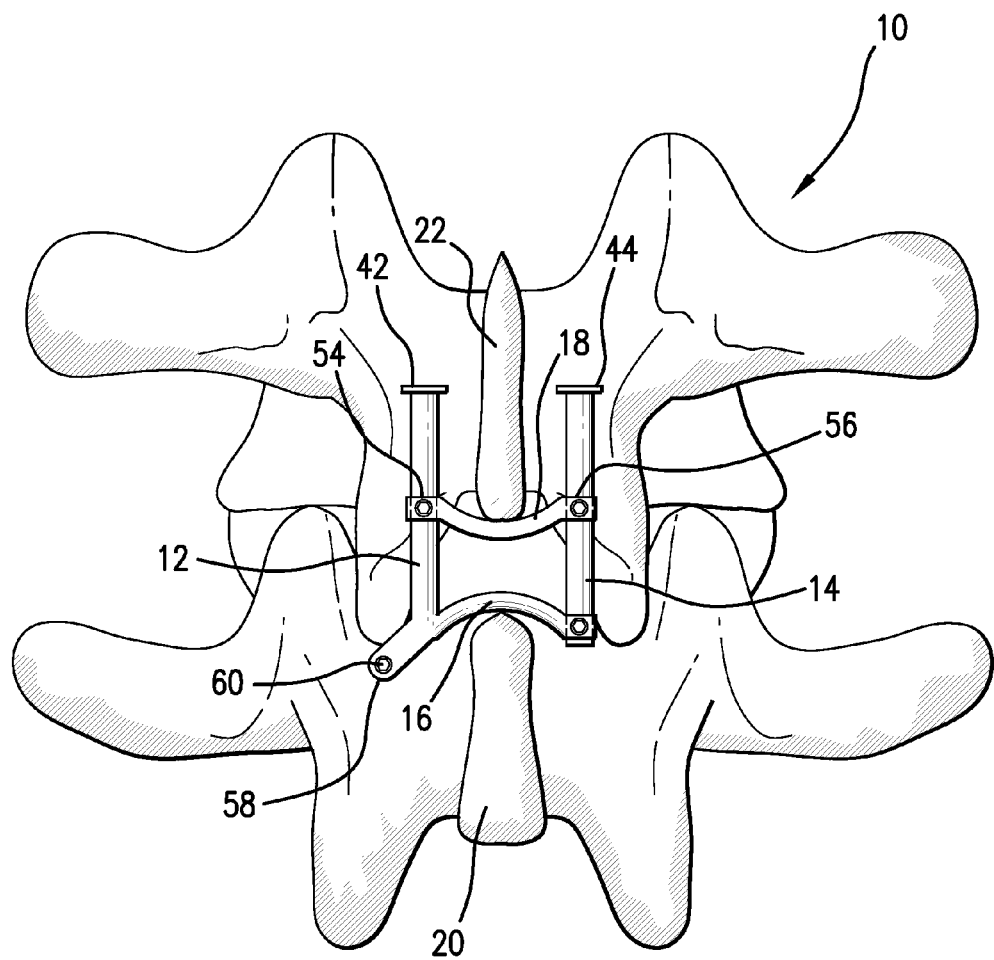
FIG. 8 shows a dorsal view of two adjacent vertebrae having the spinous process spacer device with illustrations of elements of alternative embodiments.

Alternatively, the device 10 can be configured to have longitudinal legs 12, 14 of sufficient length to overlay the dorsal surface of more than two sequentially aligned vertebrae, as shown in FIG. 2. In such a configuration, the device 10 can be provided with a respective number of adjustable transverse members 18a, 18b, 18c, and so on. When the device 10 is configured to provide an adjustable spinous process spacer for multiple aligned vertebrae, the assembly can resemble a ladder-like configuration. Importantly, when implanted in a subject the normal freedom of movement between adjacent vertebrae is maintained no matter how many sequentially aligned vertebrae are connected to the device by the multiple adjustable transverse members. As shown in FIG. 8, alternatively a device anchor element 58 can be used to provide a bone securing attachment at one or more positions at one end of the device without sacrificing the freedom of movement of adjacent vertebrae in relation to each other.

Figure 4:
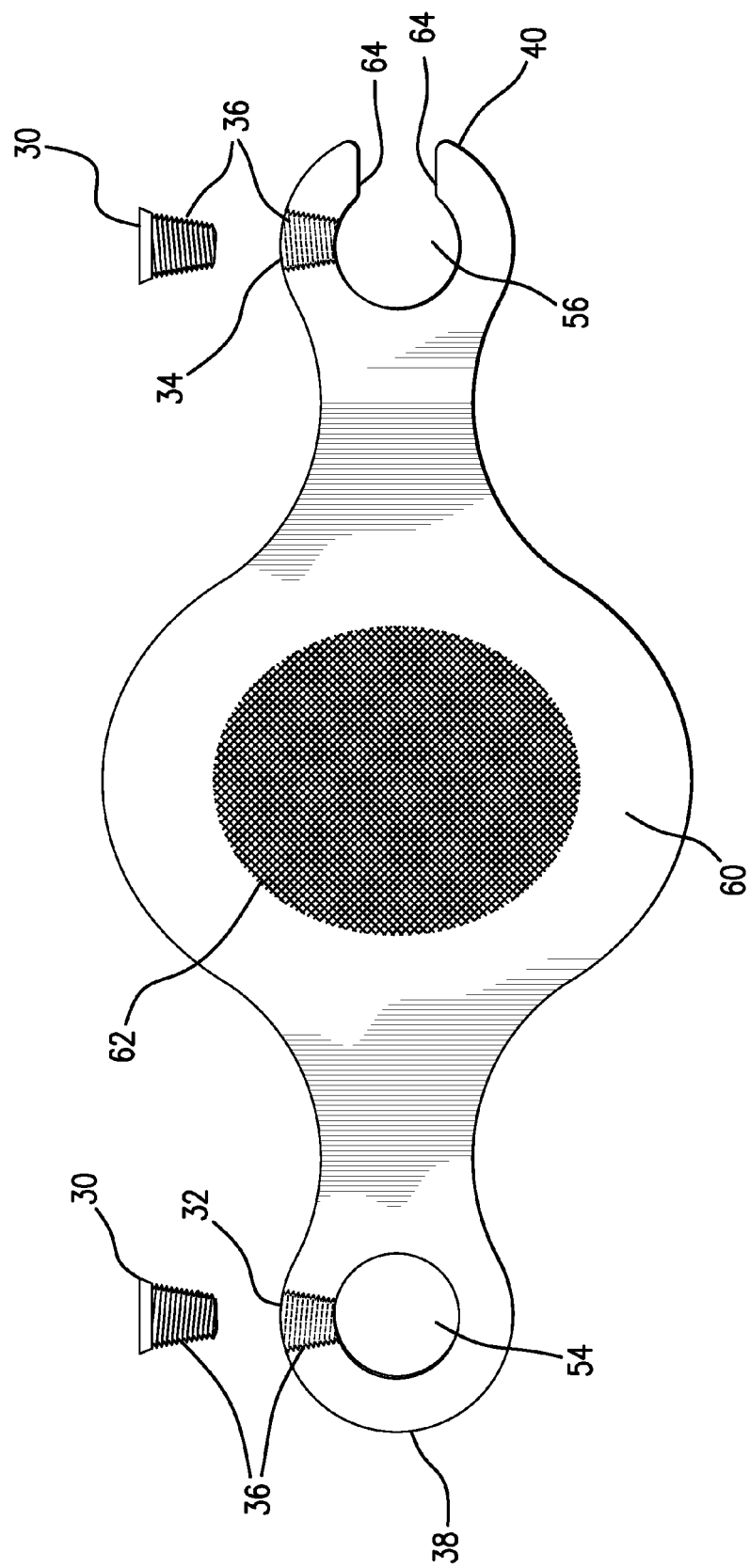
FIG. 4 shows a front view of a transverse member of the spinous process spacer device having representative illustrations of elements of alternative embodiments.
Figure 5:
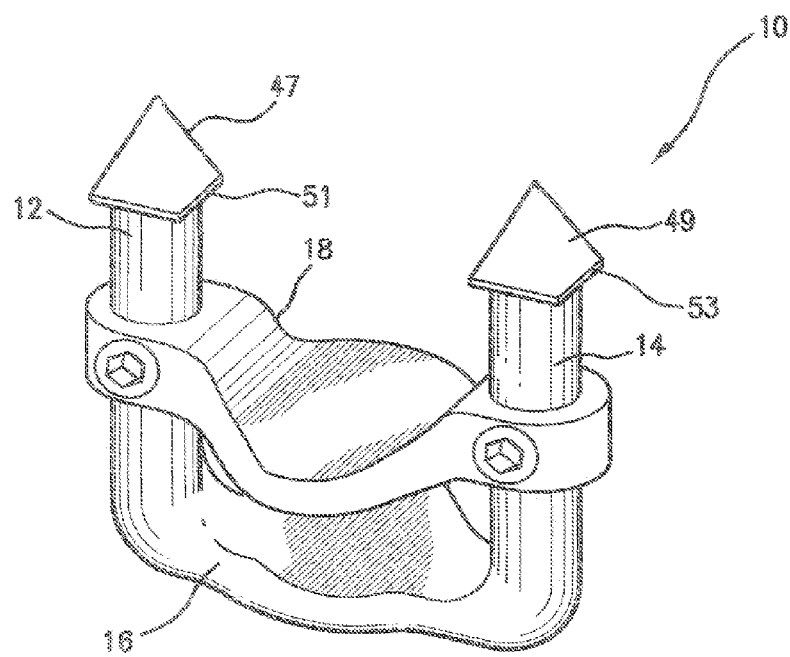
FIG. 5 shows a frontal perspective view of an embodiment of the spinous process spacer device having alternative conical or pointed leg caps.
Figure 6:
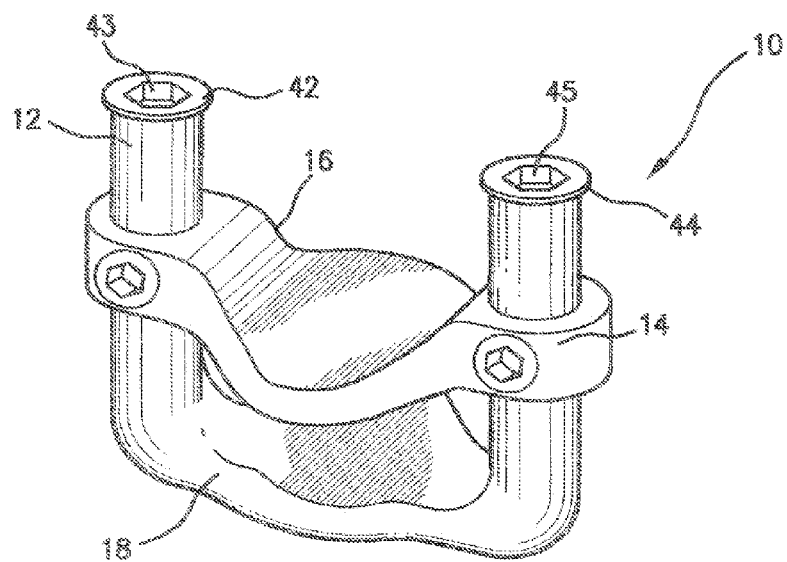
FIG. 6 shows a frontal perspective view of an embodiment of the spinous process spacer device having blunt leg cap stops and transverse members having a caudally directed inclination as compared to the device shown in FIG. 5.
Figure 7:
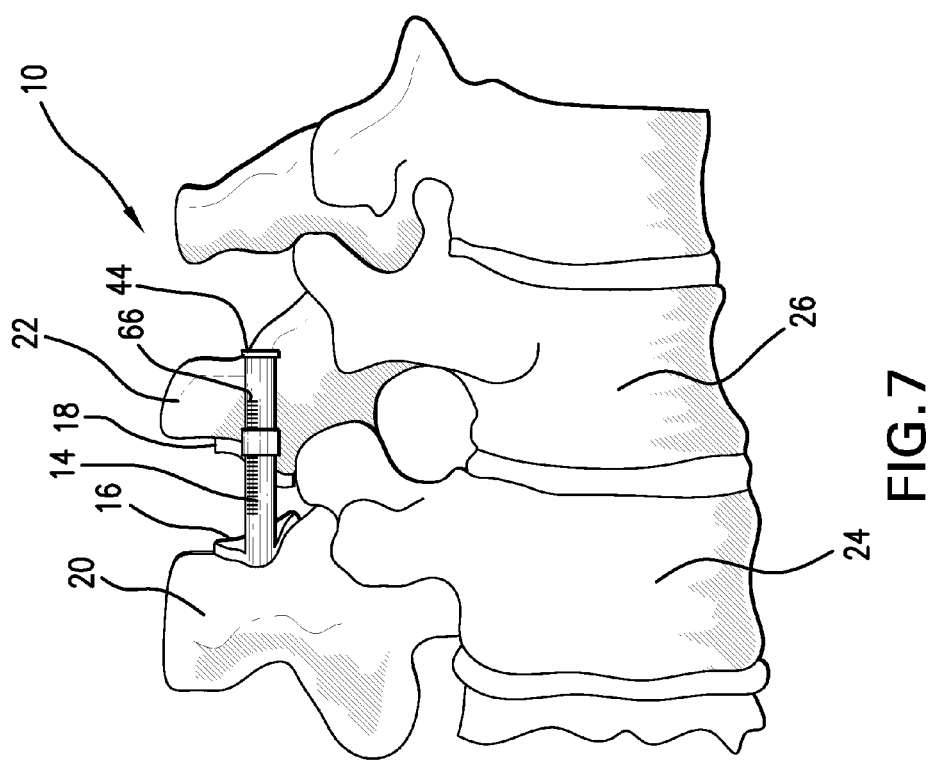
FIG. 7 shows a side view of two adjacent vertebrae having the spinous process spacer device inserted between the adjacent spinous process, the device having caudally inclining transverse members and gradation indicia on the surface of the longitudinal legs.

As best shown in FIGS. 1, 2, 3, 5, 6, 7, 8, and 9, the transverse member 16 and the adjustable transverse member 18 or multiples thereof can be configured to have a conformation designed to securely abut against a spinous process of a vertebrae and can be given an appropriate curve to help hold the spinous process 20, 22 firmly in place against the respective transverse member 16 or adjustable transverse member 18. As shown in FIG. 4, the central portion 60 of the transverse member 16 or adjustable transverse member 18 can be broadened to provide an improved contact surface for the spinous process so as to disburse the compressive forces of the device across a larger surface of the spinous process 20, 22. As shown in FIGS. 6-7, the transverse member 16 and adjustable transverse member 18 can be provided with a caudal or cephalic directed inclination of between 0 to 80 degrees, or preferably 1 to 60 degrees, or more preferably 1 to 40 degrees to better conform to the shape and inclination of the contact surface of the respective spinous processes 20, 22. Further, the contacting surface 62 of the central portion 60 of the of the transverse process 16 and adjustable transverse process 18 can be provided with a contact texture to improve the holding capability of the device against the bone surface of the spinous process 20, 22. This contact texture can be ribbed, dimpled, spiked, or of any configuration known in the art that promotes a secure contact to bone. As shown in FIG. 4, the terminal ends of the transverse member define the leg through portals 54, 56 can be of a smaller diameter than the rest of the transverse member, as shown, or can be the same as the articulating portion of the member without departing from the concept of the invention. As best shown in FIG. 7, a side view of two adjacent vertebrae with the implanted device 10, the transverse member 16 and the adjustable transverse member 18 are provided with a caudal inclination and positioned relative to the respective spinous process 20, 22 so as to maximize the holding capacity of the device 10 along the dorsal surface of the vertebrae without the need to employ multiple securing screws as are typically used in spinal surgery. For this reason, the device 10 can be implanted with relative ease using minimally invasive surgical techniques, requiring less time to complete the process, and permitting greater freedom of movement of the adjacent vertebrae relative to one another. Additionally, as shown in FIG. 7, the longitudinal legs 12, 14 can be provided with gradation indicia 66 on at least a portion of the leg surface so as to aid the surgeon in selecting the proper position for the adjustable transverse member 18 prior to securing the same to the longitudinal legs 12, 14. These indicia 66 can be marked, applied, etched, inlaid, or in any other way provided for the longitudinal legs so as to provide a visible, tactile, or radio-opaque indication of the precise location of the transverse member 16, 18 on the longitudinal leg 12, 14.

Figure 9:
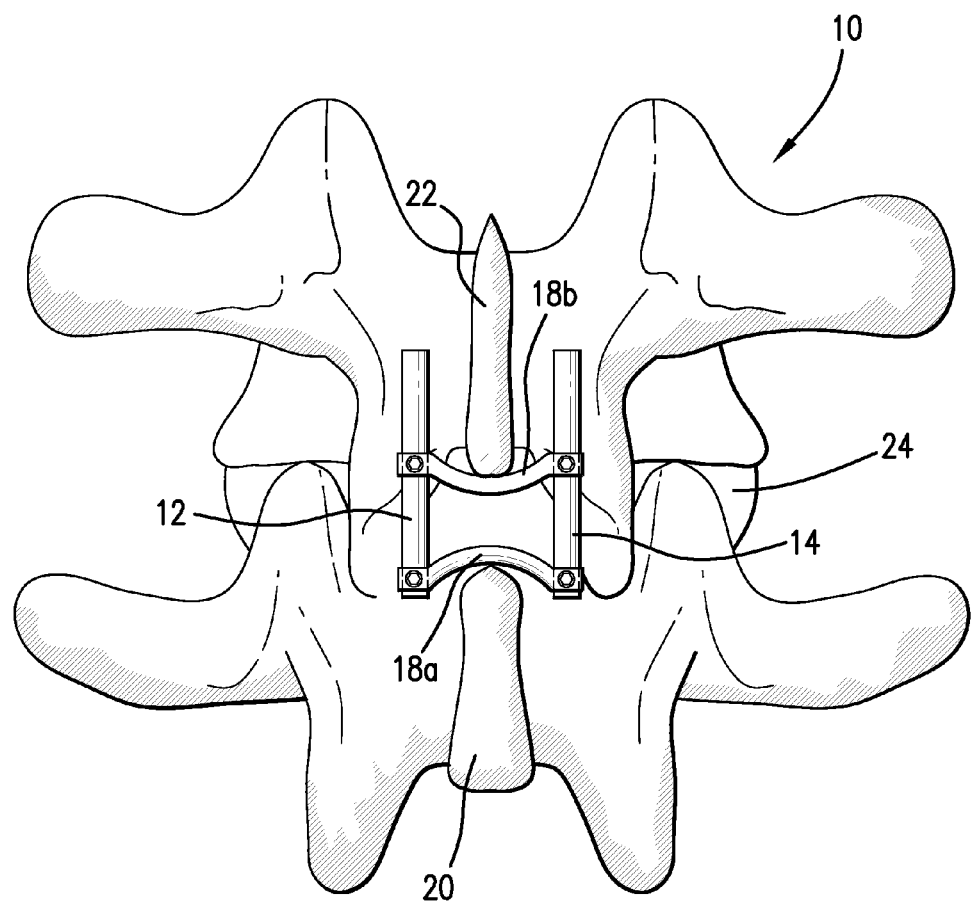
FIG. 9 shows a dorsal view of two adjacent vertebrae having the spinous process spacer device with two fully adjustable transverse members.

An alternative embodiment of the device, as shown in FIG. 8 is configured to permit sliding motion of the second longitudinal leg 14 relative to the transverse member 12. This alternative embodiment can be used as desired by the surgeon to permit greater flexibility for individual patient needs. Similarly, the alternative embodiment shown in FIG. 9 provides multiple adjustable transverse members 18a, 18b instead of a transverse member 16, as shown in FIG. 1 that is fixed to the first and second longitudinal legs 12, 14. This alternative embodiment may possibly also provide advantages to the surgeon depending upon the needs of the patient. An additional alternative connection for the longitudinal legs 12, 14 of the device 10 is shown as an example in FIG. 4 at the second end 40 of the adjustable transverse member 18. This embodiment provides an open-end longitudinal leg through portal 56. The open-end longitudinal leg through portal 56, as shown in FIG. 4, can be provided at one or both ends of the transverse member 18 and can be configured to open laterally as shown or alternatively to open superiorly or inferiorly without departing from the concept of the invention. This alternative may provide additional flexibility to the surgeon during the assembly process of the device 10. As shown in FIG. 4, the open-end through portal 56 can be provided with at least one snap fitting retaining element 64. The snap fitting can be used alone to secure the leg to the transverse member; however, it is within the concept of the invention to also provide this embodiment with a locking element 28 and locking element portal 30 to firmly secure the longitudinal leg 12, 14 is the chosen position. While the example shown in FIG. 4 is limited to only the second end 40 of the adjustable transverse member 18, it is within the concept of the invention to employ this open-end connection to facilitate connection to the first and/or second longitudinal legs 12, 14 without departing from the concept of the invention.

In practice, the device 10 is positioned, adjusted, and locked into place so as to maintain the appropriate space between the two spinal processes and thus to maintain the appropriate space between their respective vertebral bodies.

In doing so, the device serves to restrict extension of the spine and the narrowing of the space between adjacent vertebral bodies and thus limit compression of the nerve root canals and the negative neurological symptoms of spinal stenosis. Further, while the device serves to effectively restrict extension it permits normal flexion of the adjacent vertebrae in relation to each other. Importantly, the device of the present invention can be implanted in a subject in need of such treatment using minimally invasive surgical techniques. Finally, the method of implanting the device in a subject allows the supraspinal ligament to remain intact.

The device 10 can be manufactured as integral components by methods known in the art, to include, for example, molding, casting, forming or extruding, and machining processes. It is also with the inventors' conception that the component units of the invention can be manufactured of different materials and using different methods such that the materials of the unit have different tensile strengths and compression absorbance qualities prior to assembly of the unit. The components can be manufactured having a variety of different dimensions so as to provide an implantable device suitable for a variety of anatomical configurations and sizes. Manufacturing of the device components can be accomplished using suitable materials known in the art, such as, for example, implant grade metallic materials, such as titanium, titanium alloy, cobalt-chromium alloys, stainless steel, and the like. Additionally, the structures of the device 10 may be manufactured wholly or in part using non-metallic materials such as, for example, ceramic, PEEK, PEEK and artificial and natural bone materials.

It is also within the concept of the present invention to provide a kit, which includes the at least one of the devices 10, which can be provided in various sizes, as well as tools to facilitate the surgical procedure and additional orthopedic components which can be employed to permanently or temporarily stabilize the vertebrae at the surgical site if necessary. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A device for use in the treatment of spinal stenosis, comprising:
    a first longitudinal leg having a first end and a second end,
    a second longitudinal leg having a first end and a second end, said first and second legs being held approximately parallel one to the other by a transverse member connecting said first leg to said second leg at a position proximate to said first end of each respective leg, and said second ends of each of said first and second legs comprising a stop, said stop having a conical shaped end cap capable of facilitating piercing of the intraspinous ligament of a subject, and
    at least one adjustable transverse member adjustably attached to each of said first and second legs at a position selected toward said respective second end of said first and second legs, adjustable transverse member being capable of being releasably secured at said selected position on said first and second legs, said transverse member and said at least one adjustable transverse member each having a first end, a second end, and a central portion connecting said first end to said second end, said central portion being curved in a caudal or cephalic direction along substantially the length of said central portion, said curve being away from the longitudinal axis of said transverse or adjustable transverse member so as to abut against and hold in position a respective spinous process of adjacent vertebrae.

2. The device of claim 1, wherein said stop configured as a conical shaped end cap on each of said first and second leg is configured to limit the movement of the adjustable transverse member.

3. The device of claim 2, wherein said transverse member is fixedly secured to the respective first ends of said first leg and said second leg.

4. The device of claim 1, wherein said transverse member is fixedly secured to the first end of said first leg and is adjustably connected to the first end of said second leg.

5. The device of claim 1, wherein said first leg is adjustably secured to said first end of said first leg and is adjustably secured to said first end of said second leg.

6. The device of claim 1, wherein said central portion of said transverse member and said adjustable transverse member is configured to be broader than said respective first end and said second end.

7. The device of claim 1, wherein said device comprises two or more adjustable transverse members.

8. The device of claim 1, wherein said first end and said second end of said adjustable transverse member comprising a locking member portal through which a respective locking member can be releasably secured to contact and hold in place said first leg and said second leg in contact with said adjustable transverse member.

9. The device of claim 8, wherein said first leg and said second leg are in contact with said adjustable transverse member first end and second end respectively through a first and second longitudinal leg through portal, said through portals being sized and configured to allow slidable passage of said first and second legs.

10. The device of claim 9, wherein said locking member is a threaded set screw and said locking member is threadably engaged with said adjustable transverse member through a respective first and second locking member portal defined in the respective lumen wall of said longitudinal leg through portals.

11. The device of claim 1, wherein said secure contact point is a textured surface on the bone facing surface of the transverse member and adjustable transverse member.

12. The device of claim 9, wherein at least one of the through portals is an open-ended portal configured to snap fit with said respective leg.

13. The device of claim 1, wherein at least one of said connections of said first and second legs to said transverse member is an adjustable connection.

14. The device of claim 1, wherein all connections of said first and second legs to transverse members are adjustable connections.

15. The device of claim 1, wherein said first and second legs comprise graduation indicia on at least a portion of their respective surfaces.

16. The device of claim 2, wherein said stop for each of said first and second legs is releasably secured to said leg.

17. The device of claim 1, wherein at least one of said transverse member and said adjustable transverse member is inclined caudally or cephalically from a perpendicular relationship relative to said first and second legs.

18. The device of claim 17, wherein said inclination is caudally inclined at an angle between 1 to 40 degrees.

19. The device of claim 1, wherein at least a portion of at least one of said first and second legs has an approximately circular cross section so as to form a tubular shaped leg.

20. The device of claim 19, wherein at least a portion of at least one side of said tubular shaped legs have a flat surface.

21. The device of claim 1, wherein at least a portion of at least one of said first and second legs has a cross sectional configuration selected from the group consisting of oval, square, rectangular, hexagonal, and octagonal.

22. A method for treating spinal stenosis, the method comprising providing the device of claim 1,
    surgically implanting said device on the dorsal surface of at least two adjacent vertebrae, wherein said longitudinal legs of said device are positioned one on either side of the center of the spinal column and approximately parallel thereto,
    positioning the first transverse member of the device against the spinous process of a first vertebra,
    moving the adjustable transverse member to a position abutting against the spinous process of a second vertebra, the second vertebra being adjacent to the first vertebra,
    locking the adjustable transverse member into position on the two longitudinal legs so as to form an adjustably fixed spacer between the first spinous process and the second spinous process.

23. The method of claim 22, further comprising surgically implanting the device while leaving the supraspinal ligament in tact.

24. A kit for use in a surgical method to treat spinal stenosis, the kit comprising:
    at one of the devices of claim 1,
    at least one other device useful to the surgical method of implanting the device in the subject.

25. A device for use in the treatment of spinal stenosis, comprising:
    a first longitudinal leg having a first end and a second end,
    a second longitudinal leg having a first end and a second end, said first and second legs being held approximately parallel one to the other by a transverse member connecting said first leg to said second leg at a position proximate to said first end of each respective leg, and said second ends of each of said first and second legs comprising a stop, and
    at least one adjustable transverse member adjustably attached to each of said first and second legs at a position selected toward said respective second end of said first and second legs, adjustable transverse member being capable of being releasably secured at said selected position on said first and second legs, said transverse member and said at least one adjustable transverse member each having a first end, a second end, and a central portion connecting said first end to said second end, said central portion being curved in a caudal or cephalic direction along substantially the length of said central portion, said curve being away from the longitudinal axis of said transverse or adjustable transverse member so as to abut against and hold in position a respective spinous process of adjacent vertebrae.

* * * * *